United States Patent
Kraus, Jr. et al.

(10) Patent No.: US 7,232,691 B2
(45) Date of Patent: Jun. 19, 2007

(54) BIOASSAY AND BIOMOLECULAR IDENTIFICATION, SORTING, AND COLLECTION METHODS USING MAGNETIC MICROSPHERES

(75) Inventors: Robert H. Kraus, Jr., Los Alamos, NM (US); Feng Zhou, Los Alamos, NM (US); John P Nolan, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 513 days.

(21) Appl. No.: 09/995,304

(22) Filed: Nov. 27, 2001

(65) Prior Publication Data

US 2004/0002169 A1     Jan. 1, 2004

(51) Int. Cl.
*G01N 33/553*     (2006.01)
*C12Q 1/00*     (2006.01)

(52) U.S. Cl. ............... 436/526; 436/518; 436/501; 436/514; 436/50; 436/55; 436/523; 435/4; 435/287.1; 435/287.2; 435/287.3; 422/50; 422/51; 422/68.1; 422/82.05; 422/82.08; 422/186; 422/73

(58) Field of Classification Search ........... 436/518, 436/526, 501, 514, 523, 50, 55; 435/4, 287.1, 435/287.2, 287.3; 422/50, 51, 68.1, 82.05, 422/82.08, 186, 73
See application file for complete search history.

(56) References Cited

U.S. PATENT DOCUMENTS

| | | | |
|---|---|---|---|
| 5,543,289 A * | 8/1996 | Miltenyi | 435/2 |
| 5,932,097 A * | 8/1999 | Wilson | 210/222 |
| 6,432,630 B1 * | 8/2002 | Blankenstein | 435/4 |
| 6,649,403 B1 * | 11/2003 | McDevitt et al. | 435/288.5 |

* cited by examiner

*Primary Examiner*—Long V. Le
*Assistant Examiner*—Pensee T. Do
(74) *Attorney, Agent, or Firm*—Bruce H. Cottrell; Robert P. Santandrea (57) ABSTRACT

The present invention is directed to processes of separating, analyzing and/or collecting selected species within a target sample by use of magnetic microspheres including magnetic particles, the magnetic microspheres adapted for attachment to a receptor agent that can subsequently bind to selected species within the target sample. The magnetic microspheres can be sorted into a number of distinct populations, each population with a specific range of magnetic moments and different receptor agents can be attached to each distinct population of magnetic microsphere.

16 Claims, 1 Drawing Sheet

BIOASSAY AND BIOMOLECULAR IDENTIFICATION, SORTING, AND COLLECTION METHODS USING MAGNETIC MICROSPHERES

STATEMENT REGARDING FEDERAL RIGHTS

This invention was made with government support under Contract No. W-7405ENG-36 awarded by the U.S. Department of Energy. The government has certain rights in the invention.

FIELD OF THE INVENTION

The present invention relates generally to a method for identification and sorting of molecules, especially biomolecules, using receptor labeled magnetic microspheres.

BACKGROUND OF THE INVENTION

Biomedical research has evolved significantly over the past several years, with the large-scale screening of whole genomes complementing focused studies on a few genes or proteins. This evolution has encompassed applications ranging from functional analysis of unknown genes to identification of disease-related genes, screening in drug discovery and clinical diagnostics. There has been a concurrent surge in technology development to facilitate large-scale biological analysis. In general, these technologies have two components, the assay chemistry and the detection platform. Perhaps the best publicized detection platform of recent years is the flat microarray. Configured as "DNA chips," these flat microarrays offer the promise of whole genome analysis of single samples. Each element or "spot" on a flat surface array contains a target-specific receptor, for example a DNA molecule to detect a specific DNA sequence, and the signal originating from that element reports the presence of a target molecule. A related detection platform that is proving to be compatible with a range of assay chemistries in a high-throughput format is the use of encoded microparticle in combination with flow-based analysis cytometry, also known as Suspension Array Technology (SAT).

Suspension array technology employs fluorescence-encoded microspheres as array elements that bear specific receptor molecules. In SAT, microspheres having distinct optical properties, for example light scatter or fluorescence from an internal dye, are employed as solid supports for a variety of molecular analyses. By careful adjustment of these intrinsic optical properties, it is possible to prepare arrays of microspheres in which individual microsphere subsets can be identified and used to perform multiplexed analysis. Conceptually, microsphere arrays are similar to flat-surface microarrays, with distinct quanta of an intrinsic optical parameters substituting for physical location on a surface. While fluorescent- or optically-encoded microspheres have improved the flexibility of array-based analysis, that approach faces limitations in both the preparation and use of the microspheres. For example, the ability to reproducibly dye microspheres is problematic such that lot-to-lot variations in microparticles can be a problem. Moreover, the use of fluorescent dyes to encode the microparticles limits the number of analytical measurements, which also employ fluorescence detection, that can be made. An encoding method that did not require, but that was compatible with, fluorescence detection would be desirable.

The analysis of single nucleotide polymorphisms (SNPs), provides a useful example of the types of analysis that can be performed. The human genome project has shown that the DNA sequence from any two individuals is about 99.9% identical, and that the phenotypic differences between individuals are conferred largely by the 0.1% of the sequence that is different. The vast majority of this sequence variation is in the form of single nucleotide polymorphisms (or SNPs), sites in the genome where a single base varies between chromosomes in the same individual or between different individuals.

As genetic markers, SNPs have great potential for use in disease diagnostics and the discovery of new drugs. Major pharmaceutical companies and academic genome centers are involved in a major effort to discover and map SNPs. Unfortunately, conventional methods of genotyping are too slow and expensive to allow this new data to be applied on a large scale.

High throughput methods have been developed for large scale SNP scoring based on single base extension (SBE) of oligonucleotide primers using arrays of fluorescently labeled microspheres. Such systems provide accurate genotyping in a flexible format with ten-fold higher throughput and ten-fold lower costs than conventional genotyping methods. For example, U.S. Pat. No. 5,981,180 by Chandler et al. describes a method for the multiplexed diagnostic and genetic analysis of enzymes, DNA fragments, antibodies and other biomolecules. In their method, an appropriately labeled beadset is constructed, the beadset is exposed to a clinical sample, and the combined beadset/sample is analyzed by flow cytometry. Their method employs a pool of beadsets wherein beads within a subset differ in at least one distinguishing characteristic from beads in any other beadset. In that manner, the subset to which a bead belongs can be readily determined after beads from different subsets are combined. The distinguishing characteristics between beadsets are provided by incorporation of two or more fluorophores into the beads. Given suitable fluorophores and detection equipment, use of multiple fluorophores could expand the multiplexing power of the system.

However, the multiplexed analysis capacity of typical fluorescent microsphere arrays is currently limited to one hundred simultaneous assays, and expansion beyond this number involves a number of technical challenges. In addition, the routine preparation of these fluorescent microspheres still presents problems.

Solid phase arrays have also been used for the rapid and specific detection of multiple polymorphic nucleotides. Typically, an allele-specific hybridization probe is linked to a solid support and a target nucleic acid (e.g., a genomic nucleic acid, an amplicon, or, most commonly, an amplified mixture) is hybridized to the probe. Either the probe, or the target, or both, can be labeled, typically with a fluorophore. Where the target is labeled, hybridization is detected by detecting bound fluorescence. Where the probe is labeled, hybridization is typically detected by quenching of the label. Where both the probe and the target are labeled, detection of hybridization is typically performed through monitoring of a color shift resulting from proximity of the two bound labels. A variety of labeling strategies, labels, and the like, particularly for fluorescent based applications are described.

In one embodiment, an array of probes is synthesized on a solid support. Exemplary solid supports include glass, plastics, polymers, metals, metalloids, ceramics, organics, and the like. Using chip masking technologies and photoprotective chemistry it is possible to generate ordered arrays of nucleic acid probes. These arrays, which are known, e.g., as "DNA chips," or as very large scale immobilized polymer arrays (VLSIPS™ arrays) can include millions of defined probe regions on a substrate having an area of about 1 cm² to several cm², thereby incorporating sets of from a few to millions of probes. The construction and use of solid phase nucleic acid arrays to detect target nucleic acids is well described in the literature. See, e.g., Fodor et al. (1991) Science, 251: 767-777; Hubbell U.S. Pat. No. 5,571,639; and, Pinkel et al. PCT/US95/16155 (WO 96/17958).

Magnetic particles made from magnetite and inert matrix materials have long been used in the field of biochemistry. Such particles generally range in size from a few nanometers up to a few microns in diameter and may contain from 15% to 100% magnetite. They are often described as superparamagnetic particles or, in the larger size range, as beads. The usual methodology is to coat the surface of the particles with some biologically active material that will cause them to bond strongly with specific chemical species, microscopic objects or particles of interest (e.g., proteins, viruses, and DNA fragments). The particles then become "handles" by which the objects can be moved or immobilized using a magnetic gradient, usually provided by a strong permanent magnet. U.S. Pat. No. 4,537,861 by Elings et al. describes an example of tagging using magnetic particles. Specially constructed fixtures using rare-earth magnets and iron pole pieces are commercially available for this purpose. However, in this process, magnetic particles are never used in labeled subsets of particles allowing for a multiplexed assay of a sample.

In another approach using magnetic particles, U.S. Pat. No. 5,252,493 by Fujiwkara et al. describes a ultra-sensitive laser magnetic immunoassay method including: labeling an antigen or antibody with micro-particles of a magnetic substance to form a magnetic-labeled body; subjecting a specimen and the magnetic-labeled body to an antigen-antibody reaction to form a reacted body-specimen complex; separating and removing unreacted body from the reacted complex; guiding and concentrating the reacted complex magnetically; irradiating the concentrated complex with a laser beam; detecting outgoing light from a measurement system to provide a quantitative result in the picogram range. Again in this process, magnetic particles are never used in labeled subsets of particles allowing for a multiplexed assay of a sample.

It would be beneficial if another method were available for detecting the presence of a sought-after, predetermined target, e.g., such as a nucleotide sequence or allelic variants. It would further be beneficial if such a detection method were capable of providing multiple analyses in a single assay (multiplex assays).

SUMMARY OF THE INVENTION

In accordance with the purposes of the present invention, as embodied and broadly described herein, the present invention includes a process of separating a sample including attaching a different receptor agent to at least two distinct populations of magnetic microspheres with a specific range of magnetic moments, combining a target sample with the distinct populations of magnetic microspheres containing the different attached receptor agents together for a period of time sufficient for binding between attached receptor agents and target species within the target sample to form one or more receptor agent-target species complexes, and, sorting the distinct populations of magnetic microspheres containing the different receptor agent-target species complexes by passage through a magnetic separator. In one embodiment of this process, the process of separating further includes analyzing, for formation of one or more receptor agent-target species complexes within the target sample, each of the sorted distinct populations of magnetic microspheres containing the different attached receptor agents. In one embodiment of this process, the distinct populations of magnetic microspheres with a specific range of magnetic moments are obtained from a process which includes forming magnetic microspheres including magnetic particles, the magnetic microspheres adapted for attachment to a receptor agent; and sorting the magnetic microspheres by passage through a magnetic separator so as to separate the magnetic microspheres into a number of distinct populations of magnetic microspheres, each distinct population with a specific range of magnetic moments.

The present invention also includes a process of analyzing a sample including attaching a different receptor agent to at least two distinct populations of magnetic microspheres with a specific range of magnetic moments, combining a target sample with the distinct populations of magnetic microspheres containing the different attached receptor agents together for a period of time sufficient for binding between receptor agents and a target species within the target sample to form one or more receptor agent-target species complexes, individually passing the magnetic microspheres in a fluid microsphere suspension into a flow channel and past a magnetic measurement system capable of measuring the magnetic moment of each individual magnetic microsphere so as to identify to which distinct population each suspended magnetic microsphere belongs, and, analyzing individual magnetic microspheres in a detection system for detectable properties of receptor agent-target species complexes so as to measure a detectable property of receptor agent-target species complexes. In one embodiment of this process, the process includes, prior to any initial sorting stage, passing the magnetic microspheres through a magnetic field so as to magnetize the magnetic microspheres. In another embodiment of this process, the process includes after an initial sorting stage and prior to combining a target sample with the number of distinct populations of magnetized, magnetic microspheres containing the different attached receptor agents, demagnetizing the magnetized, magnetic microspheres. In a still further embodiment of this process, the process includes passing the magnetic microspheres containing the different attached receptor agents in the flow channel through a magnetic field so as to re-magnetize the magnetic microspheres. In yet another embodiment of this process, the process includes passing the magnetic microspheres containing the different attached receptor agents through an alignment field so as to orient the magnetic microspheres in a predetermined direction within the fluid microsphere suspension. In one embodiment of this process, the distinct populations of magnetic microspheres with a specific range of magnetic moments are obtained from a process which includes forming magnetic microspheres including magnetic particles, the magnetic microspheres adapted for attachment to a receptor agent; and sorting the magnetic microspheres by passage through a magnetic separator so as to separate the magnetic microspheres into a number of distinct populations of magnetic microspheres, each distinct population with a specific range of magnetic moments.

The present invention further includes a process of collecting a sample including attaching a different receptor agent to at least two distinct populations of magnetic microspheres with a specific range of magnetic moments, combining a target sample with the distinct populations of magnetic microspheres containing the different attached receptor agents together for a period of time sufficient for binding between receptor agents and a target species within the target sample to form one or more receptor agent-target species complexes, individually passing the magnetic microspheres in a fluid microsphere suspension into a flow channel and past a magnetic measurement system capable of measuring the magnetic moment of each individual magnetic microsphere so as to identify to which distinct population each suspended magnetic microsphere belongs, and, collecting individual magnetic microspheres of at least one distinct population of magnetic microspheres. In one embodiment of this process, the process includes, prior to any initial sorting stage, passing the magnetic microspheres through a magnetic field so as to magnetize the magnetic microspheres. In another embodiment of this process, the process includes after an initial sorting stage and prior to combining a target sample with the number of distinct populations of magnetized, magnetic microspheres containing the different attached receptor agents, demagnetizing the magnetized, magnetic microspheres. In a still further embodiment of this process, the process includes passing the magnetic microspheres containing the different attached receptor agents in the flow channel through a magnetic field so as to re-magnetize the magnetic microspheres. In yet another embodiment of this process, the process includes passing the magnetic microspheres containing the different attached receptor agents through an alignment field so as to orient the magnetic microspheres in a predetermined direction within the fluid microsphere suspension. In one embodiment of this process, the distinct populations of magnetic microspheres with a specific range of magnetic moments are obtained from a process which includes forming magnetic microspheres including magnetic particles, the magnetic microspheres adapted for attachment to a receptor agent; and sorting the magnetic microspheres by passage through a magnetic separator so as to separate the magnetic microspheres into a number of distinct populations of magnetic microspheres, each distinct population with a specific range of magnetic moments.

DETAILED DESCRIPTION

The present invention is concerned with: developing and fabricating a unique flow system for fractionation of magnetic particles or magnetic microspheres; performing substantially simultaneous measurements for magnetization and another detectable property such as fluorescence in a flow cytometry-like system for assay of qualitative and/or quantitative characteristics of a sample; and performing multiplexed analysis of a sample, e.g., for multiplexed genotyping using a parallel magnetic sorting system.

The processes of this invention can be used together with the apparatus and kits described by Kraus, Jr. et at., in U.S. patent application Ser. No. 09/995,302, filed concurrently herewith, entitled "Apparatus Used in Identification, Sorting and Collection Methods Using Magnetic Microspheres and Magnetic Microsphere Kits," now abandoned; and U.S. Patent Application U.S. patent application Ser. No. 10/851, 019, filed May 21, 2004, entitled "Apparatus Used in Identification, Sorting and Collection Methods Using Magnetic Microspheres and Magnetic Microsphere Kits," which is a divisional application of U.S. patent application Ser. No. 09/995,302. Such description is incorporated herein by reference.

Within the present description, the term "microparticle" is meant to refer to small particles, generally from about 0.01 microns to about 1000 microns, that include an inherent property (e.g., magnetization, fluorescence and the like) allowing identification of each microparticle as belonging to a specific group. The term "microsphere" is meant to refer to a particle within the range of from about 0.01 microns to about 1000 microns consisting of one or more identifying tags (e.g., magnetization, fluorescence and the like) formed together with a polymer, glass, or other matrix, coating or the like. The term "magnetic microsphere" is meant to refer to a particle within the range of from about 0.01 microns to about 1000 microns including one or more magnetic domains with a polymer, glass, or other matrix, coating or the like. Neither the term "microsphere" or "magnetic microsphere" is meant to exclude shapes other than spherical, and such terms are meant to include other shapes such as globular and the like. The term "receptor" is meant to refer to a molecule or molecular fragment that is bound or otherwise attached to the surface of a microsphere.

In addition to different magnetic properties, i.e., magnetic moments, the microspheres in the present invention can have an additional detectable property. Such a detectable property can be, e.g., fluorescence, absorbance, reflectance, scattering and the like. Analytical equipment is commercially available to detect and determine each of these type properties. For example, flow cytometry systems are available employing laser based systems for detection and measurement of the fluorescence of a microsphere as it passes the detector.

Magnetic microsphere arrays and the instrumentation to analyze such arrays represent a major breakthrough in large-scale genomic analysis. Magnetic microsphere arrays consisting of a thousand elements (and potentially many more) can be prepared, and a flow cytometer can measure both fluorescence (e.g., by standard known techniques) and magnetization (using, e.g., Superconducting Quantum Interference Device (SQUID) technology or other magnetic detection technology) to provide greatly enhanced analysis capabilities. In essence, the magnetic microsphere array technology of the present invention serves as a bar-coding system to provide a detectable label to each microsphere. The processes of the present invention uses magnetic microspheres incorporating magnetic particles to "label" different assay agents. Such magnetic microspheres can be uniquely identified by their magnetic moment, M, by either measuring the moment directly or using a "spectrometer-like" apparatus described below. It is estimated that for magnetic microspheres of a size from about 10 nanometers (nm) to about 5 millimeters (mm), a system can be devised with between $10^2$ and $10^4$ separable bins. Generally, the present processes involve several basic steps: 1) magnetic microsphere preparation; 2) separation of magnetic microspheres into populations with specific magnetizations; 3) attachment of receptor agents to magnetic microspheres; 4) incubation of the magnetic microspheres; and, 5) analysis of magnetic microspheres and quantitative measurement of fluorescence (assay).

Magnetic particles can be obtained from a large variety of vendors. Investigating a relatively small number (much less than 100) of different simultaneous receptor agents can tolerate some variety of particle size and shape without interfering with the performance of the sorting process. Investigating large numbers of receptor agents simultaneously will require a greater number of particles, and greater uniformity of particle size and shape to prevent variations in drag from interfering in the sorting process. This can be readily accomplished by encapsulating the magnetic particles inside a glass or organic polymer coating to form microspheres or beads of uniform size. For example, magnetic particles can be encapsulated in polystyrene and provide a suitable surface for subsequent attachment of receptor agents. Encapsulation in uniformly sized and spherical glass and polymer beads is a commercially available technology. Although not required, the magnetic particles preferably will initially have little or no magnetization (remnant field), and thus have very little dipole moment or mutual attraction. Any coating or encapsulation of the magnetic particles (except for specific receptor agents) is preferably applied prior to the magnetic particle sorting. After encapsulation, magnetic particles are thereafter generally referred to as magnetic microspheres.

In addition to encapsulation or coating for forming magnetic microspheres, the magnetic microspheres can be formed by imbedding magnetic particles within or on a surface of an organic polymer material or glass. The magnetic particles may protrude beyond the surface of the organic polymer material or glass. Similarly, the magnetic microspheres can be formed by immobilizing magnetic particles within or on a surface of an organic polymer material or glass. The magnetic particles may protrude beyond the surface of the organic polymer material or glass. Another manner of forming magnetic microspheres can involve coating magnetic particles with a material having first reactive functionality and reacting the coated magnetic particles with non-magnetic microspheres having a second reactive functionality that reacts with the first reactive functionality to form microspheres having the required magnetic component. Among suitable reactive functionalities are included functionalities, e.g., from the group of amines, carboxylates, and epoxies. Additionally, affinity pairs such as biotin-avidin and the like that form a complex can be used as the first and second reactive functionalities. Thus, both covalent binding and non-covalent interaction approaches may be employed.

Typically, the magnetic particles used in forming the magnetic microspheres will be of a size between about 1000 micron (µm) and 10 nanometers, although both smaller and larger particles may be used in some instances. The lower limit in size is likely about 10 nanometers (nm), although the required size may vary depending upon the chemical composition of the magnetic particles. In general, bigger particle sizes can be preferred as they provide greater surface area and volume for binding capacity. This can provide greater variety in magnetization through volume of the particles. In one embodiment for practicing the present invention, the utilized magnetic microspheres are preferably of the same dimensions to minimize fluid dynamic effects during subsequent sorting steps.

The suitable chemical compositions for the magnetic particles are generally ferromagnetic materials and include rare earth containing materials such as, e.g., iron-cobalt, iron-platinum, samarium-cobalt, neodynium-iron-boride, and the like. Other magnetic materials, e.g., superparamagnetic materials such as iron oxides ($Fe_3O_4$) may be used as well. Among the preferred magnetic materials are included iron-cobalt as such material is generally easier to magnetize, has a stronger magnetization (about 1.7 Tesla) and is less susceptible to corrosion.

The range in magnetic moment of the magnetic particles is generally $10^{-22}$ and $10^{-15}$ T-m$^3$, more preferably above $10^{-21}$ T-m$^3$. This magnetic moment is essentially maintained after formation of the magnetic microspheres as the coating does not affect the magnetic moment detectable by SQUID technology or other magnetic detection technologies. Magnetic moments of particles within the range indicated above are easily detected and measured by commercially available SQUID sensors at sub-millimeter to a few millimeter sensor-to-particle separations.

In practicing the present invention, the magnetic particles, preferably as magnetic microspheres after coating, are initially separated into populations with specific magnetizations. A fluid suspension of the magnetic microspheres is introduced into the apparatus schematically shown in FIG. 1. This magnetic field particle fractionation flow device 10 enables the sorting of magnetic microspheres according to their magnetization. The suspended microspheres pass through magnetization coils 12 to magnetize the microspheres which then flow into the spectrometer chamber 14 where they follow trajectories determined largely by the magnetic moment, M, of each microsphere under the influence of, e.g., magnet 18 (one manner of providing the necessary magnetic field gradient), and are collected in magnetic microsphere collection bins 16. Such collection bins could be tubes. System performance parameters such as the number of different collection bins, sorting resolution, and signal-to-noise between adjacent bins are variable over orders of magnitude depending on system size, engineering tolerances, and the like. Preferably, there is a high resolution between magnetic microspheres with differing magnetic moments. Optionally, magnetic microsphere flow can be terminated and magnetic microspheres in each bin are collected after sorting the desired number of magnetic microspheres. Magnetic microspheres are captured within the collection bins by the field from the spectrometer magnetic field and do not rely upon the flow to maintain the separation.

Figure 1:
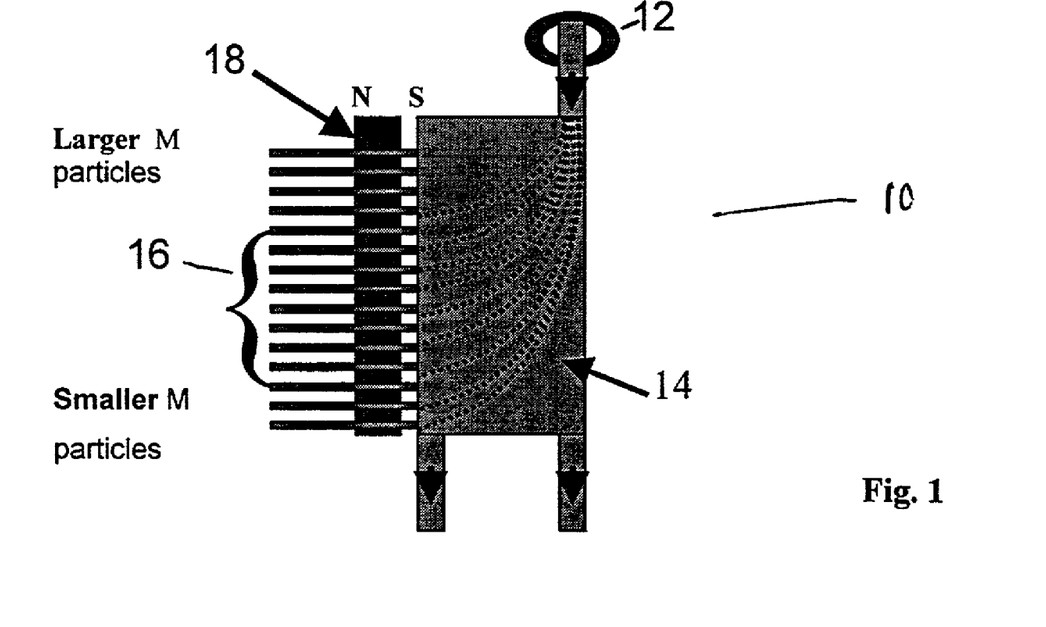
FIG. 1 shows a schematic drawing of a particle sorting apparatus for sorting of magnetic particles or magnetic microspheres by magnetic moment, M, in accordance with the present invention.

The peak field of the magnetizing magnet is chosen to assure saturation magnetization is reached for the specific magnetic particles being used (e.g., the saturation field for Sm—Co is significantly greater than that for magnetite). Although a number of different magnetization systems can be employed, a suitable example is a series of "thin" pulsed solenoid magnets. The magnitude and duration of the solenoid pulse would be tuned to the specific type of magnetic material being used for the particles. The field profile of neighboring solenoids would overlap to assure all particles are magnetized. This is easily assured since the typical time to assure magnetization is on the order of a millisecond or less. The series of solenoids would be activated from the most upstream magnet. The next downstream magnet will be activated at time $t=T_M$ before the upstream magnet is deactivated, where $T_M$ is the magnetization time for the given magnetic particles. This algorithm assures all particles are magnetized. Since the distance traveled by the particles in the fluid flow during the time required magnetizing them, $D_M$, is far smaller than the solenoid field length, only two or three solenoids will be required in the series. After the last (downstream) solenoid is activated, the first (upstream) solenoid is activated again after a delay equal to the transit time of particles through the entire solenoid series field less $2 \times T_S$, where $T_S$ is the time required to activate all the magnets in the solenoid series as described above. Thus the delay is:

$$\text{Activation Delay} = L_S/V_F - (2 \times T_S)$$

where $L_S$ is the total length of the solenoid series field (above the particle magnetization threshold), and $V_F$ is the fluid flow velocity. This fairly complex magnetization method is designed to prevent the magnetic particles from being attracted by a strong and constant field gradient that would necessarily result from the magnetizing magnets. In systems and situations where there is a sufficient flow rate to prevent the magnetic particles from being attracted out of the flow, a single pulsed or continuous magnetizing field would be far simpler to implement.

Magnetic shielding should be provided between the magnetic microsphere spectrometer chamber and the flow tube. Such shielding will eliminate the possibility of the magnetization fields from the solenoid from interfering with particle motion in the spectrometer chamber and to prevent fields from the spectrometer magnetic from interfering with particle motion prior to entering the spectrometer chamber.

The magnetized microspheres experience a force within the spectrometer chamber proportional to the particle magnetic moment, M, and move along a trajectory that is determined by the magnetic force on the particle, the fluid flow, and drag. Techniques used in flow cytometry are employed to generate a uniform fluid flow throughout the chamber. Uniform flow within the spectrometer chamber is more important when the process is for identification and assay instead for sort and assay, both described below. In the application where the spectrometer is used to sort the magnetic microspheres a second time after combining a target sample with the number of distinct populations of magnetic microspheres containing the different attached receptor agents together for a period of time sufficient for binding between attached receptor agents and target species within the target sample to form one or more receptor agent-target species complexes, the requirement of uniform flow can be relaxed provided that flow through the chamber is reproducible in successive applications of the sorting step. Any effects of a non-uniform flow will cancel out between the first and second sorting steps.

Magnetic microspheres are collected in tubes (see FIG. 1) and captured by the field of the spectrometer magnet. The separation (shown in the figure) between collection tubes is exaggerated for clarity. The number and size in the separation system preferably has collection tubes adjoining one another with minimal wall thickness. In one embodiment, walls between the orifices to the collection tubes are tapered to knife-edges helping prevent magnetic microspheres from collecting on the ends of the walls. Flow through the collection tubes would further facilitate keeping magnetic microspheres from accumulating at the orifices of the tubes.

There are numerous engineering requirements and design variables involved for design of this system including the fluid flow velocity, range of particle magnetic moments, range of particle sizes, desired size of the apparatus, numbers of bins desired (system resolution), particle throughput for the system, and the like. Such variables are well known by those skilled in the art.

In one embodiment, the magnetic microspheres are demagnetized prior to proceeding on to the next step. This can be readily accomplished by heating above the material Curie point as is well known to those skilled in the art. Demagnitized microspheres are easier to work with because there is significantly less tendency to aglomerate. Alternatively, the magnetic microspheres remain magnetized while proceeding on to the next step. Experience has shown that any aglomerated microspheres can be easily separated by several simple methods such as ultrasonication of the samples.

Next, attachment of the receptor agents to the magnetic microspheres is conducted. Once the magnetic microspheres are "sorted," the bins that are collected are maintained separately. A different receptor agent (or assay agent) can be attached to magnetic microspheres from each retained bin. Once the receptor is attached, an investigator can simply choose the amount of each receptor agent (attached to different magnetic microsphere groups) to introduce into the medium being investigated. For purposes of genotyping applications, the receptor is preferably a synthetic oligonucleotide of DNA covalently attached to the magnetic microsphere surface. The receptor agent is generally of, e.g., nucleic acids such as, e.g., DNA, RNA and nucleotides, proteins such as, e.g., antibodies, antigens and peptides, lipids, carbohydrates, synthetic polymers or any other specific receptor molecules. The receptor agent is generally specific in binding to a particular target species or class of target species. The receptor agent may be attached to the magnetic microsphere surface by various methods including, but not limited to, physical adsorption, specific binding, or chemical conjugation.

The present invention is useful in a wide number of applications. A number of potential applications follow and other applications will be readily apparent to those skilled in the art. For example, in one embodiment in accordance with the present invention, analysis of target samples can be conducted. In another embodiment in accordance with the present invention, sorting of target samples can be conducted.

Analysis may be carried out on biological systems or other samples such as chemical systems. For analysis of biological systems, a receptor agent can be, e.g., an immobilized molecule of DNA, including cDNA and oligonucleotides, an immobilized molecule of RNA, an immobilized protein (including an antibody, an antigen and a peptide), an immobilized lipid, an immobilized carbohydrate, an immobilized sugar or an immobilized synthetic polymer. Use of an immobilized molecule of DNA as receptor agents can allow specific assays, e.g., for single nucleotide polymorphisms (SNPs), for sequencing validation, for genotyping, for bacteria identification, for DNA-based tissue typing, for multiplexed viral load analysis, for gene expression, for DNA-protein interaction, and for molecular assembly. Use of an immobilized molecule of RNA as receptor agents can allow specific assays, e.g., for RNA-protein interaction, and for molecular assembly. Use of an immobilized protein molecule as the receptor agent can allow specific assay, e.g., for protein expression, immunoassay, immunoprecipitation, biomarker discovery, protein-protein interaction, for protein-DNA interactions, for protein-RNA interactions, or for protein-other molecule interactions; for antibody-antigen interactions. Use of an immobilized lipid as the receptor agent can allow for a specific assay in the form of biosensors, for molecular assembly and for lipid-other molecule interaction.

Examples of potential immunoassay applications include but are not limited, e.g., to: detection of antibodies specific for both proteinase 3 (PR3) and myeloperoxidase (MPO), such detection important in the diagnosis of systemic vasculitis; an assay for simultaneous detection of serum IgG responses to *Toxoplasma gondii*, rubella virus, cytomegalovirus, and herpes simplex virus types 1 and 2; an assay for the simultaneous multiplexed assay quantifying human serum IgG1, IgG2, IgG3, IgG4, IgA and IgM in a single tube; allergy testing; autoimmune testing; epitope-mapping; multiplexed analysis of human cytokines; a multiplexed array for measurement of human chorionic gonadotropin (hCG) and alpha-fetoprotein (aFP); and, pneumococcal assay to measure antibodies to the 23-serotype pneumococcal capsular polysaccharides (PPS).

Examples of potential gene expression or protein expression applications include but are not limited to, e.g., identification of distinctive expression patterns characteristic of selected physiological and pathological states, and screening for subtle changes in response to various stimuli or environmental change.

Examples of potential biomarker discovery include but are not limited to search for schizophrenia diagnostic markers, kidney stone disease markers, prostrate cancer markers, validation of protein markers and the like.

Examples of potential antibody-antigen interaction applications include but are not limited to, e.g., antigen capture and identification for antibodies or antibody capture and identification for antigens.

Examples of potential protein-protein interaction applications include but are not limited to, e.g., capture and purification of a potential ligand for use as a receptor agent, measurement accurate intact mass of a captured analyte, and identification of a captured analyte by "on-bead" peptide mapping.

In another application, the present invention may also allow for the sorting of multiple cells, protein, DNA fragments, RNA fragments and other molecules.

A standard flow cytometry system can be used to analyze the fluorescence from any particular microsphere. It is well known how to form a sequential flow steam of particles for use in a flow cytometer or similar sensitive fluorescence detection apparatus. See, e.g., U.S. Pat. No. 3,710,933 by Fulwyler et al. and Flow Cytometry and Sorting, 2nd Ed., ed. M. R. Melamed et al. Wiley-Liss, New York, 1990, incorporated herein by reference. Basically, a dilute solution of magnetic microspheres is formed to a low concentration effective to provide the microspheres spaced apart in the flow stream so that only a single microsphere is present in the excitation and detection volume. The solution of magnetic microspheres is then introduced into a laminar sheath flow stream for passage through the detection chamber for light excitation of a single microsphere at a time. The flow rates of the sample and the sheath can be adjusted to maintain separation between microspheres and to provide the optimum time for each microsphere in the excitation source.

In one embodiment of the present invention, the analytical instrumentation includes the standard flow cytometry parts for analysis of the fluorescence (as the detectable property) of the individual microspheres in combination with the necessary magnetic measurement system, e.g., SQUIDs, for measurement of the magnetic characteristics of the individual microspheres. SQUIDs can be positioned in close proximity to the chamber for fluorescence measurement such that substantially simultaneous fluorescence and magnetization measurements can be performed. By "substantially simultaneous" it is meant to indicate that the correlation between magnetic and fluorescence measurements for any given particle is unambiguous with respect to neighboring particles in the flow stream. That is, passage of an individual magnetic microsphere past SQUID sensors can allow for identification, through detection of the magnetic moment, of a particular subset of microspheres to which each individual microsphere belongs. That can be coupled with the standard fluorescence measurements from the receptor agents on each subset of magnetic microspheres. In this manner the present invention can allow for use of the flow cytometer and magnetic microsphere arrays to perform multiplexed genetic analysis.

In the practice of the present invention, a mixture of magnetic microspheres with attached receptor agents is combined with the medium being investigated and incubated as appropriate. In some cases the medium is treated with some combination of reagents to generate a fluorescent complex that can be captured onto the magnetic microspheres. Such reagents may include an antibody or other ligand, an oligonucleotide or analogue, or other molecule with specific binding or enzymatic activity. In other cases, the receptors attached to the magnetic microspheres are themselves fluorescent and report the presence of analyte as a change in fluorescence. For the genotyping applications, a DNA polymerase-mediated extension of oligonucleotide primers with fluorescent nucleotide analogues can be used that have successfully performed on fluorescent microspheres.

The incubation media is prepared for use in one of the two flow systems used to perform the final particle identification and fluorescent measurements. The two methods for sorting the magnetic microspheres and assaying the efficiency and/or effectiveness of the agents of interest are described below.

Figure 2:
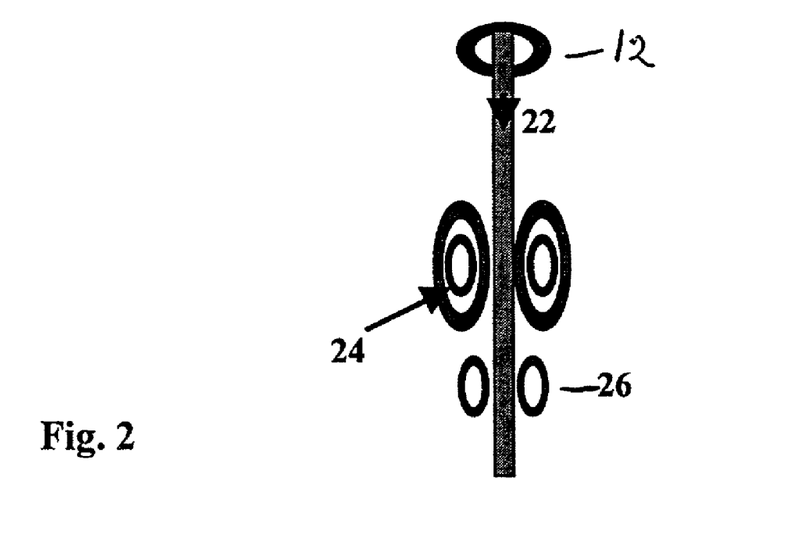
FIG. 2 shows a schematic drawing of an apparatus for single particle based analysis and analytical scale sorting in accordance with the present invention.

In one embodiment of the present invention, the method simultaneously identifies magnetic microspheres based on magnetic moment and measures another detectable property, e.g., the fluorescence, associated with each magnetic microsphere. By "identification", it is meant that a particular magnetic microsphere can be associated to belong to a specific sorted group based on the magnetic moment of the particle and accordingly be known to have a particular magnetic label. It is important to note that an absolute measurement of the magnetic moment of the microsphere is not required, rather a relative measurement with sufficiently high resolution to uniquely associate the particle with a specific sorted group of microspheres. A schematic of this method is shown in FIG. 2. A suspension of magnetic microspheres is introduced into a sheath stream 22 that hydrodynamically focuses the sample stream in a flow cell. The magnetic moment, M, of the magnetized microspheres is measured by a SQUID array 24 as individual microspheres flow past the sensors (preferably at least two). In one embodiment, a microsphere-aligning field can be used that orients the particles passing under the SQUID, but does not couple to the SQUID (e.g., the field is tangential to the SQUID). In one embodiment, at least two SQUID sensors can be required, one on either side of the flow channel to correct for microsphere position within the flow cell. Small High-$T_C$ SQUID sensors will be used for this purpose with a dewar designed to minimize the SQUID-flow cell distance, similar to the SQUID microscope described by Epsy et al., in IEEE Trans. Appl. Superconductivity, v. 9, p. 3692 (1999). Minimizing the SQUID-flow channel distance will improve the sensitivity of the sensor to microsphere field, and reduce the relative magnitude of superposed field from neighboring microspheres (e.g., error). The typical microsphere separation in flow systems currently in use is on the order of centimeters, more than enough to prevent any appreciable superposition of field from neighboring microspheres. If needed, moment corrections can easily be calculated on the basis of moment and proximity of first and even second nearest neighbors. Typical fields of the magnetic microspheres at the SQUID sensors are expected to be easily detectable 1-100,000 picoTesla (pT) for 1-5 micron (μm) magnetic microspheres of high remnant field materials assuming 3 mm sensor-microsphere separation (readily attainable). After the relative measurement of M, the fluid carries the magnetic microsphere past a laser/sensor apparatus 26 to perform the fluorescence measurement. Several different fluorescence emission signals may be collected from each microsphere. Analysis of the correlated magnetization and fluorescence data can then be performed. As with conventional fluorescence-activated cell sorting, single magnetic microsphere measurements can be used to control the physical sorting of individual magnetic microspheres. While this approach to sorting enables very specific criteria to be applied to sort decisions, it is generally restricted to sorting two to four populations and is fairly low throughput.

In another embodiment of the present invention, the method utilizes the same sorting method to separate the magnetic microspheres into bins as was implemented in Step 2. After incubation, the suspension of magnetic microspheres is introduced into the apparatus shown in FIG. 1. This method has at least three significant advantages over the first described embodiment: 1) magnetic microspheres can be sorted at a much higher rate; 2) a much broader range of magnetic microspheres can be used; and 3) systematic errors in the sorting (e.g. flow uniformity, particle size and shape, etc.) will largely cancel. The identification method measures the relative particle |M| requiring well-separated magnetic microspheres. While not problematic for applications that require only particle analysis, these constraints represent significant limitations for preparative sorting applications. The spectrometer sorting method is capable of sorting a fluid flow containing a particle density that is orders of magnitude larger than in the identification scheme, limited only the requirement that neighboring magnetic microspheres do not impart an appreciable force on one another.

Once the magnetic microspheres are sorted into their respective bins, the quantitative fluorescence assay is performed using the established methods. The suspended particles flow past a laser/detector system that identifies the desired bound states. Two basic system approaches can be developed: a two-stage method or a single-stage continuous flow process. Alternately, the analyte bound to the receptor on the magnetic microspheres can be analyzed off-line by some other analytical method (mass spectrometry, NMR, and the like). The ability to perform preparative-scale purification of biomolecules is an especially important feature of this second sorting method.

A new approach in performing assay experiments, e.g., bioassay experiments, is also presented by this invention. The basic approach is to use magnetic microspheres as addressable solid supports in bioassay experiments. Magnetic microspheres from about 10 nm to about 10 μm in size or more can be obtained with a continuous range of magnetic moments from near zero to upper limits that depend on the material (or materials) chosen. The number of separation bins that could partition the magnetic microspheres is determined by engineering considerations, but ranges from a low range of about 100 to up to a high range of about 1 million. For very large numbers of bins, two-stage sorting is preferable as described above to be practical. The ability to address large numbers of solid supports, each of which bears a different receptor, would enable the performance of highly parallel multiplexed analysis of many analytes simultaneously. This method can be adapted to both high throughput assay analysis systems such as that described above, or extremely high throughput physical sorting devices as also described above. The present invention provides an instrument platform to enable many types of genomic and biochemical analysis on a scale not currently possible.

The variation in size and shape will be small enough to allow at least several subpopulations of magnetic microspheres to be identified. For very highly multiplexed applications, uniform spherical glass beads or polymer beads containing magnetic particles may have less variation in size and shape, allowing more specific populations to be identified.

The principle of this magnetic microsphere separation technique is similar to that of continuous flow electrophoresis, a widely used preparative separation method, except that the electric field is replaced with a magnetic field. Instrumentation for continuous flow separation are described in the literature (see, e.g., J. Chromatography B 722:121-139 (1999)) and are commercially available. Modification of such designs to enable magnetic separation is well within the capabilities of one skilled in the art.

Immobilization of biomolecules as receptors on microsphere surfaces is well known to those skilled in the art. There are several conjugation chemistries available for the attachment of synthetic DNA to the surface of polystyrene or glass surfaces.

Several assay systems have been developed involving microspheres and flow cytometry, including the detection of DNA from pathogenic bacteria and the identification of SNPs associated with chronic beryllium disease. Such systems can be used.

The sensitivities of the fluorescence detection and SQUID sensing are well within the range required for the measurement of single magnetic microspheres. The main hurdles will be engineering issues associated with the integration of a magnetically shielded SQUID sensor in close proximity to the laser light source and light collection optics to enable dual magnetization and fluorescence measurements to be made on single magnetic microspheres in the flowing sample stream of the flow cytometer.

In one aspect of the invention a pool of magnetic microsphere subsets is employed. The individual subsets are prepared so that magnetic microspheres within a subset are relatively homogeneous but can be differentiated in magnetic moment characteristic from magnetic microspheres in any other subset. Therefore, the subset to which a magnetic microsphere belongs can readily be determined after magnetic microspheres from different subsets are pooled. A magnetic microsphere's subset identity can be verified during flow cytometric analysis of the pool in a single assay step and in real-time.

Prior to pooling subsets of magnetic microspheres to form a beadset, the magnetic microspheres within each subset can be coupled to a reactant that will specifically react with a given analyte of interest in a fluid sample to be tested. Usually, different subsets will be coupled to different reactants so as to detect different analytes. For example, subset 1 may be labeled so as to detect analyte A (AnA); subset 2 may be labeled so as to detect analyte B (AnB); and so forth.

At some point prior to assay, the variously labeled subsets are pooled. The pooled magnetic microspheres, or beadset, are then mixed with a fluid sample to test for analytes reactive with the various reactants bound to the magnetic microspheres. The system is designed so that reactions between the reactants on the magnetic microsphere surfaces and the corresponding analytes in the fluid sample will cause changes in the intensity of at least one additional fluorescent signal ($F_m$) emitted from a fluorochrome that fluoresces at a distinct wavelength. The $F_m$ signal serves as a "measurement signal," that is, it indicates the extent to which the reactant on a given magnetic microsphere has undergone a reaction with its corresponding analyte. The $F_m$ signal may result from the addition to the assay mixture of a fluorescently labeled "secondary" reagent that binds to the magnetic microsphere surface at the site where a reactant-analyte reaction has occurred.

When the mixture (pooled magnetic microspheres and fluid sample) is run through a flow cytometer, each magnetic microsphere is individually examined.

The magnetic moments are measured and used to classify each magnetic microsphere into the subset to which it belongs and, therefore, identify the analyte that the magnetic microsphere is designed to detect. The $F_m$ value of the magnetic microsphere is determined to indicate the concentration of analyte of interest in the fluid sample. Not only are many magnetic microspheres from each subset rapidly evaluated in a single run, multiple subsets are evaluated in a single run. Thus, in a single-pass and in real-time a sample is evaluated for multiple analytes. Measured $F_m$ values for all magnetic microspheres assayed and classified as belonging to a given subset may be averaged or otherwise manipulated statistically to give a single meaningful data point, displayed in histogram format to provide information about the distribution of $F_m$ values within the subset, or analyzed as a function of time to provide information about the rate of a reaction involving that analyte.

In one embodiment, the magnetic microspheres will have two or more fluorochromes incorporated within or on them so that each of the magnetic microspheres in a given subset will possess at least four different classification parameters, e.g., $C_1$, $C_2$, $C_3$, and $C_4$. For example, the magnetic microspheres may be made to contain a red fluorochrome ($C_3$), such as nile red, and bear an orange fluorochrome ($C_4$), such as Cy3 or phycoerythrin. A third fluorochrome, such as fluorescein, may be used as a source of the $C_n$ or $F_m$ signal. As those of skill in the art will recognize, additional fluorochromes may be used to generate additional $C_n$ signals. That is, given suitable fluorochromes and equipment, those of skill in the art may use multiple fluorochromes to measure a variety of $C_n$ or $F_m$ values, thus expanding the multiplexing power of the system even further.

In certain applications designed for more quantitative analysis of analyte concentrations or for kinetic studies, multiple subsets of magnetic microspheres may be coupled to the same reactant but at varying concentrations so as to produce subsets of magnetic microspheres varying in density of bound reactant rather than in the type of reactant. In such an embodiment, the reactant associated with classification parameter $C_4$, for example, may be incorporated directly into the reactive reagent that is coupled to the magnetic microspheres, thereby allowing $C_4$ conveniently to serve as an indicator of density of reactant on the magnetic microsphere surface as well as an indicator of reactant identity.

To prepare subsets varying in reactant density one may, for example, select, isolate, or prepare a starting panel of different subsets of magnetic microspheres, each subset differing from the other subsets in one or more of $C_1$, $C_2$, or $C_3$. Each of those subsets may be further subdivided into a number of aliquots. Magnetic microspheres in each aliquot may be coupled with a reactant of choice that has been fluorescently labeled with a fluorochrome associated with $C_4$ (e.g., Analyte A labeled with Cy3) under conditions such that the concentration or density of reactant bound to the magnetic microspheres of each aliquot will differ from that of each other aliquot in the subset. Alternatively, an entire subset may be treated with the $C_4$ fluorochrome under conditions that produce a heterogeneous distribution of $C_4$ reactant on magnetic microspheres within the subset. The subset may then be sorted with a cell sorter on the basis of the intensity of $C_4$ to yield further subsets that differ from one another in $C_4$ intensity.

One limitation of the alternative embodiment of using $C_4$ labeled reactant as a classification agent is that one must design the system so that the value of $C_4$ as a classification parameter is not lost. Therefore, one must take care to assure that the $C_4$ intensities of all subsets carrying reagent A differs from the $C_4$ intensities of all subsets carrying reagents B, C, and so forth. Otherwise, $C_4$ would not be useful as a parameter to discriminate reactant A from reactant B, and so forth.

With either embodiment, the number of subsets that can be prepared and used in practice of the invention is theoretically quite high, but in practice will depend on the level of homogeneity within a subset and the precision of the magnetic measurements that can be obtained. Magnetic microsphere subsets may be subjected to flow cytometric sorting or other procedures at various different points in preparation or maintenance of the magnetic microsphere subsets to increase homogeneity within the subset. Of course, with simple assays designed to detect only a few different analytes, more heterogeneity can be allowed within a subset without compromising the reliability of the assay.

In an illustrative embodiment set forth here to explain one manner in which the invention can work in practice, the magnetic microspheres are used to test for a variety of antibodies in a fluid sample. A panel of magnetic microsphere subsets having known varying $C_1$, $C_2$, $C_3$, and $C_4$ values is first prepared or otherwise obtained. The magnetic microspheres within each subset are then coupled to a given antigen of interest. Each subset receives a different antigen. The subsets are then pooled to form an assay beadset and may be stored for later use and/or sold as a commercial test kit. In the assay procedure, the magnetic microspheres are mixed with the fluid to be analyzed for antibodies reactive with the variety of antigens carried on the magnetic microspheres under conditions that will permit antigen-antibody interaction. The magnetic microspheres can be labeled with a "secondary" reagent that binds to antibodies bound to the antigens on the magnetic microspheres and that also bears the measurement fluorochrome associated with parameter $F_m$ (e.g., fluorescein). A fluoresceinated antibody specific for immunoglobulin may be used for this purpose. The magnetic microspheres are then run through a magnetic detection system and then a flow cytometer, and each magnetic microsphere is classified by its characteristic magnetic moment. At the same time, the presence of antibodies specific for antigen A, B, etc., can be detected by measuring green fluorescence, $F_m$, of each magnetic microsphere. The magnetic moment allow one to determine the subset to which a magnetic microsphere belongs, which serves as an identifier for the antigen carried on the magnetic microsphere. The $F_m$ value of the magnetic microsphere indicates the extent to which the antibody reactive with that antigen is present in the sample.

Although the present invention has been described with reference to specific details, it is not intended that such details should be regarded as limitations upon the scope of the invention, except as and to the extent that they are included in the accompanying claims.

What is claimed is:

1. A process of separating a sample comprising:

attaching a different receptor agent to at least two distinct populations of magnetic micro spheres with a specific range of magnetic moments, wherein each of said magnetic microspheres includes a plurality of magnetic particles, and wherein said magnetic particles are either coated, imbedded in said magnetic microspheres, or immobilized on a surface of or within said magnetic microspheres;

combining a target sample with said distinct populations of magnetic microspheres containing the different attached receptor agents together for a period of time sufficient to allow for binding between attached receptor agents and target species within said target sample to form one or more receptor agent-target species complexes; and, sorting said distinct populations of magnetic microspheres containing the different receptor agent-target species complexes by passing said magnetic microspheres through a first magnetic field provided by a first magnet for magnetizing said magnetic microspheres to a chamber and a collector, wherein the chamber and the collector are disposed in a second magnetic field provided by a second magnet, and wherein said magnetic microspheres having different magnetic moments are separated in the chamber in the presence of the second magnetic field according to trajectories determined by their respective magnetic moments.

2. The process of claim 1 further including analyzing, for formation of one or more receptor agent-target species complexes within said target sample, each of said sorted distinct populations of magnetic microspheres containing the different attached receptor agents.

3. The process of claim 1 wherein said distinct populations of magnetic microspheres with a specific range of magnetic moments are obtained from a process comprising forming magnetic microspheres including magnetic particles, said magnetic microspheres attachable to a receptor agent; and sorting said magnetic microspheres by passage through a magnetic separator so as to separate said magnetic microspheres into a number of distinct populations of magnetic microspheres, each distinct population with a specific range of magnetic moments.

4. The process of claim 3 wherein the step of sorting said distinct populations of magnetic microspheres further includes passing said magnetic microspheres through a magnetic field so as to magnetize said magnetic microspheres prior to sorting said distinct populations.

5. The process of claim 1 wherein said magnetic microspheres are of a size of from about 0.01 micron to about 1000 microns.

6. The process of claim 1 wherein said magnetic microspheres are of substantially the same dimensions.

7. The process of claim 1 wherein said magnetic microspheres include magnetic particles of a material selected from the group consisting of a ferromagnetic material and a superparamagnetic material.

8. The process of claim 6 wherein said magnetic particles are selected from the group consisting of iron-cobalt, iron-platinum, and samarium-cobalt.

9. The process of claim 7 wherein said magnetic microspheres include magnetic particles and a coating material of a material selected from the group consisting of an organic polymeric material and glass.

10. The process of claim 7 wherein said magnetic microspheres include magnetic particles and a coating material of polystyrene.

11. The process of claim 1 wherein said receptor agents are selected from the group consisting of antigens, antibodies, peptides, proteins, nucleic acids, lipids, carbohydrates and enzymes.

12. The process of claim 1 wherein said magnetic particles are coated with a material selected from the group consisting of an organic polymeric material and glass.

13. The process of claim 1 wherein said magnetic particles are imbedded within a material selected from the group consisting of an organic polymeric material and glass.

14. The process of claim 1 wherein said magnetic particles are immobilized on a surface of or within a material selected from the group consisting of an organic polymeric material and glass.

15. The process of claim 1 further including the step of forming said magnetic micro spheres including said magnetic particles, wherein forming said magnetic microspheres including said magnetic particles comprises:

coating said magnetic particles with a material having a first reactive functionality; and, reacting said coated magnetic particles with non-magnetic microspheres having a second reactive functionality, wherein said second reactive functionality reacts with said first reactive functionality to form said magnetic microspheres including said magnetic particles.

16. The process of claim 15 wherein said first reactive functionality is selected from the group consisting of amines, carboxylates, epoxies and one of an affinity pair, and said second reactive functionality is different from said first reactive functionality and is selected from the group consisting of amines, carboxylates, epoxies, and the other of the affinity pair.

* * * * *